United States Patent [19]
Friese et al.

[11] Patent Number: 5,846,391
[45] Date of Patent: Dec. 8, 1998

[54] SEAL FOR A SENSOR ELEMENT OF A GAS SENSOR

[75] Inventors: Karl-Hermann Friese, Leonberg; Helmut Weyl, Schwieberdingen; Hans-Martin Wiedenmann, Stuttgart; Anton Hans, Ludwigsburg, all of Germany

[73] Assignee: Robert Bosch GmbH, Stuttgart, Germany

[21] Appl. No.: 836,425

[22] PCT Filed: Mar. 21, 1996

[86] PCT No.: PCT/DE96/00567

§ 371 Date: Apr. 29, 1997

§ 102(e) Date: Apr. 29, 1997

[87] PCT Pub. No.: WO97/08542

PCT Pub. Date: Mar. 6, 1997

[30] Foreign Application Priority Data

Aug. 30, 1995 [DE] Germany .................. 195 32 090.5

[51] Int. Cl.⁶ .................................................. G01N 27/407
[52] U.S. Cl. .................. 204/424; 204/426; 204/428; 277/192; 277/193; 277/227
[58] Field of Search ................... 204/421–429; 277/192, 193, 227

[56] References Cited

U.S. PATENT DOCUMENTS

| | | | |
|---|---|---|---|
| 3,891,529 | 6/1975 | Beesch | 204/428 |
| 4,383,906 | 5/1983 | Sano et al. | 204/428 |
| 4,569,748 | 2/1986 | Yamakawa et al. | 204/428 |
| 4,732,663 | 3/1988 | Kato et al. | 204/428 |
| 4,956,072 | 9/1990 | Kojima et al. | 204/428 |
| 5,329,806 | 7/1994 | McClanahan . | |
| 5,571,397 | 11/1996 | Weber . | |

FOREIGN PATENT DOCUMENTS

| | | |
|---|---|---|
| 0 398 579 | 11/1990 | European Pat. Off. . |
| 0 406 531 | 1/1991 | European Pat. Off. . |
| 39 22 331 | 1/1991 | Germany . |
| 4318789 | 12/1994 | Germany . |
| 92 08127 | 5/1992 | WIPO . |

Primary Examiner—T. Tung
Attorney, Agent, or Firm—Spencer & Frank

[57] ABSTRACT

A seal for a sensor element for a gas sensor for determining the oxygen content in a gas to be measured including exhaust gases of internal combustion engines, the seal including a metallic housing having defined therein a longitudinal bore; a sensor element inserted into the longitudinal bore; and a sealing arrangement provided in the longitudinal bore, surrounding at least a portion of the sensor element, and comprised of at least one seal element comprised of steatite and an additional seal element comprised of boron nitride arranged in contact with one another and in a stack having a side near the gas to be measured so that, when there is one seal element comprised of steatite, the one seal element comprised of steatite is positioned on the side of the stack near the gas to be measured, and so that, when there are two seal elements comprised of steatite, the additional seal element is positioned between the two seal elements comprised of steatite, wherein the at least one seal element comprised of steatite and the additional seal element comprised of boron nitride are inserted into the longitudinal bore of the housing as deformable rings and are pressed-in therein, and wherein, during the pressing-in, the deformable rings are deformed in such a way that the at least one seal element comprised of steatite and the additional seal element comprised of boron nitride are pushed against the sensor element and the housing.

10 Claims, 3 Drawing Sheets

SEAL FOR A SENSOR ELEMENT OF A GAS SENSOR

BACKGROUND OF THE INVENTION

The invention starts with a seal for a sensor element of a gas sensor according to the generic type in the Main claim. Such a seal is known from the DE-OS 43 18 789 where the sensor element is arranged in a longitudinal bore of a housing by means of two seal elements and an additional, deformable seal that is arranged between the seal elements. The two seal elements consist of magnesium-aluminum silicate (steatite). Rough-pressed metal powder or graphite is listed as material for the additional seal.

SUMMARY OF THE INVENTION

The inventive seal The present invention is a seal for a sensor element for a gas sensor, in particular for determining the oxygen content in exhaust gases of internal combustion engines, which seals the sensor element in a longitudinal bore of a metallic housing, characterized in that a sealing arrangement is provided, which comprises at least two seal elements, arranged one above the other, and that the one seal element is composed of boron nitride and the other seal element of steatite has the advantage that it is gas-tight as well as impermeable for liquids, in particular fuel, and additionally has a high temperature resistance.

Through the measures listed in the dependent claims, advantageous modifications of the seal described in the Main claim are possible. An easy handling of the seal during assembly is achieved if as sealing rings the steatite seal elements are inserted in the presintered condition and the boron nitride seal element is inserted in the hot-pressed condition and if these are deformed during the assembly through the effects of a force in such a way that the seal element material conforms to the sensor element, and the housing and the sensor element is thus kept gas-tight inside the housing.

BRIEF DESCRIPTION OF THE DRAWINGS

Three embodiments of the invention are shown in the drawing and are explained in more detail in the following description.

DESCRIPTION OF THE PREFERRED EMBODIMENTS

Figure 1:
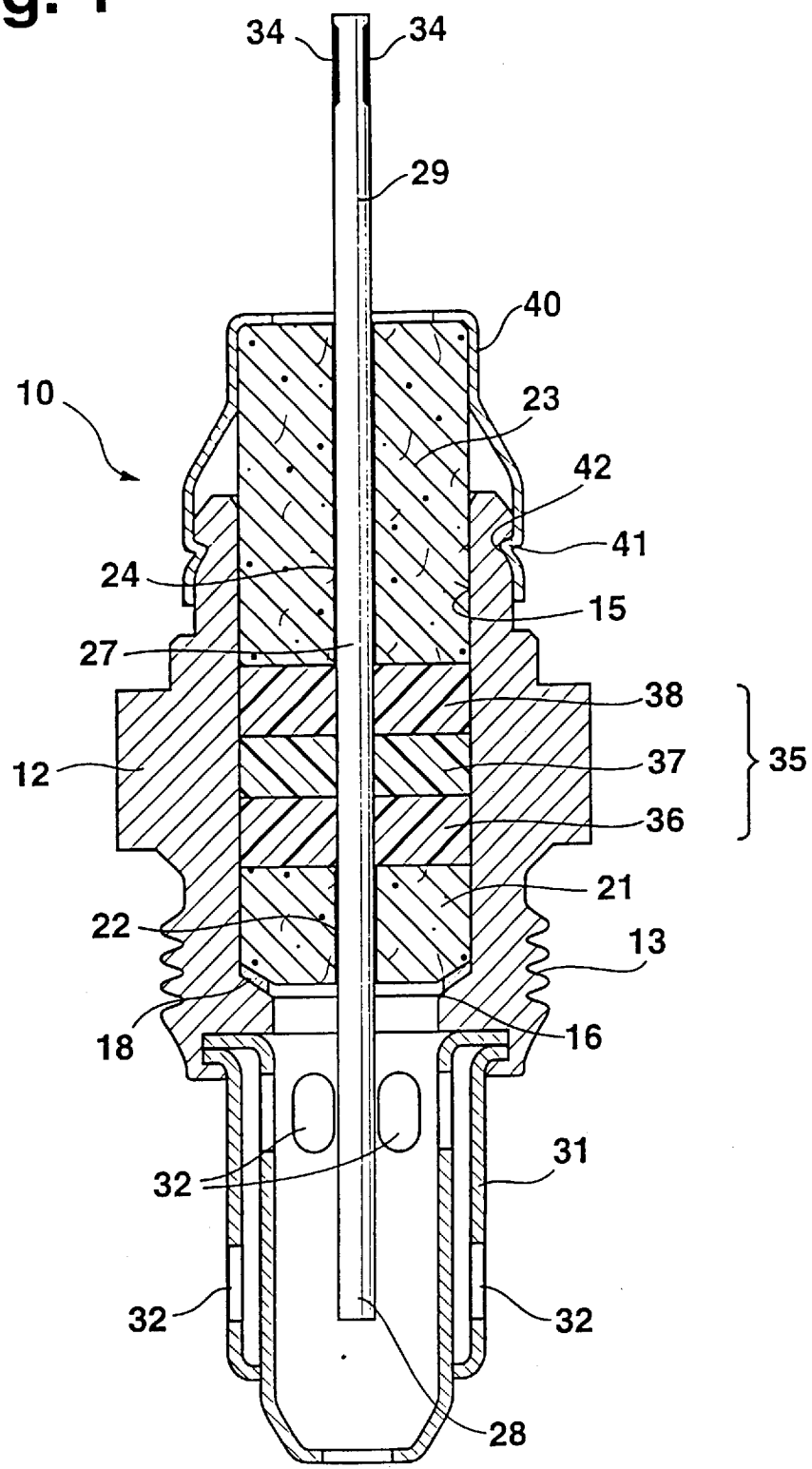
FIG. 1 shows a cross section through a gas sensor with a sealing arrangement according to a first exemplary embodiment, FIG. 2 the gas sensor with a sealing arrangement according to a second exemplary embodiment, and FIG. 3 the gas sensor with a sealing arrangement according to a third exemplary embodiment.
Figure 2:
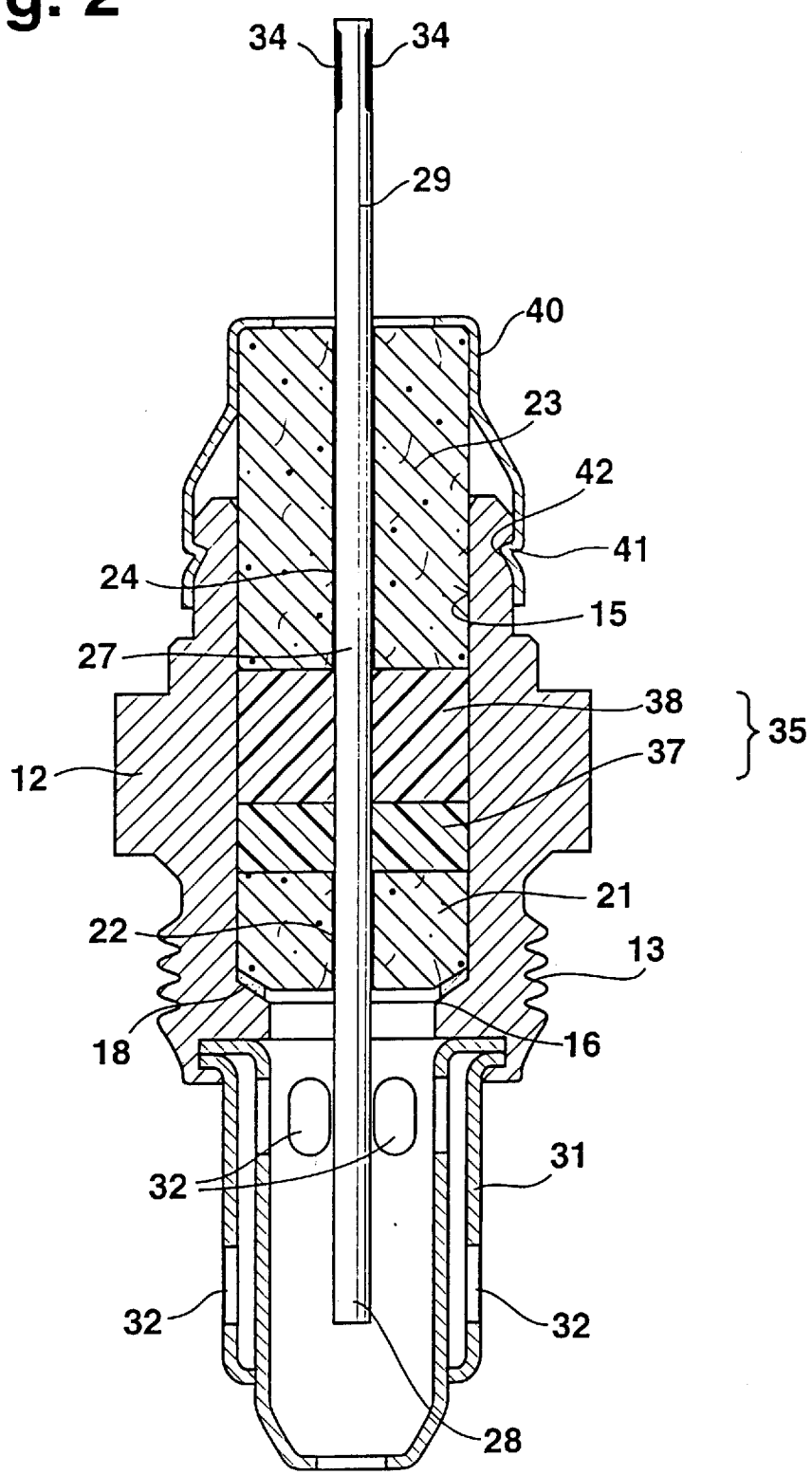
Figure 3:
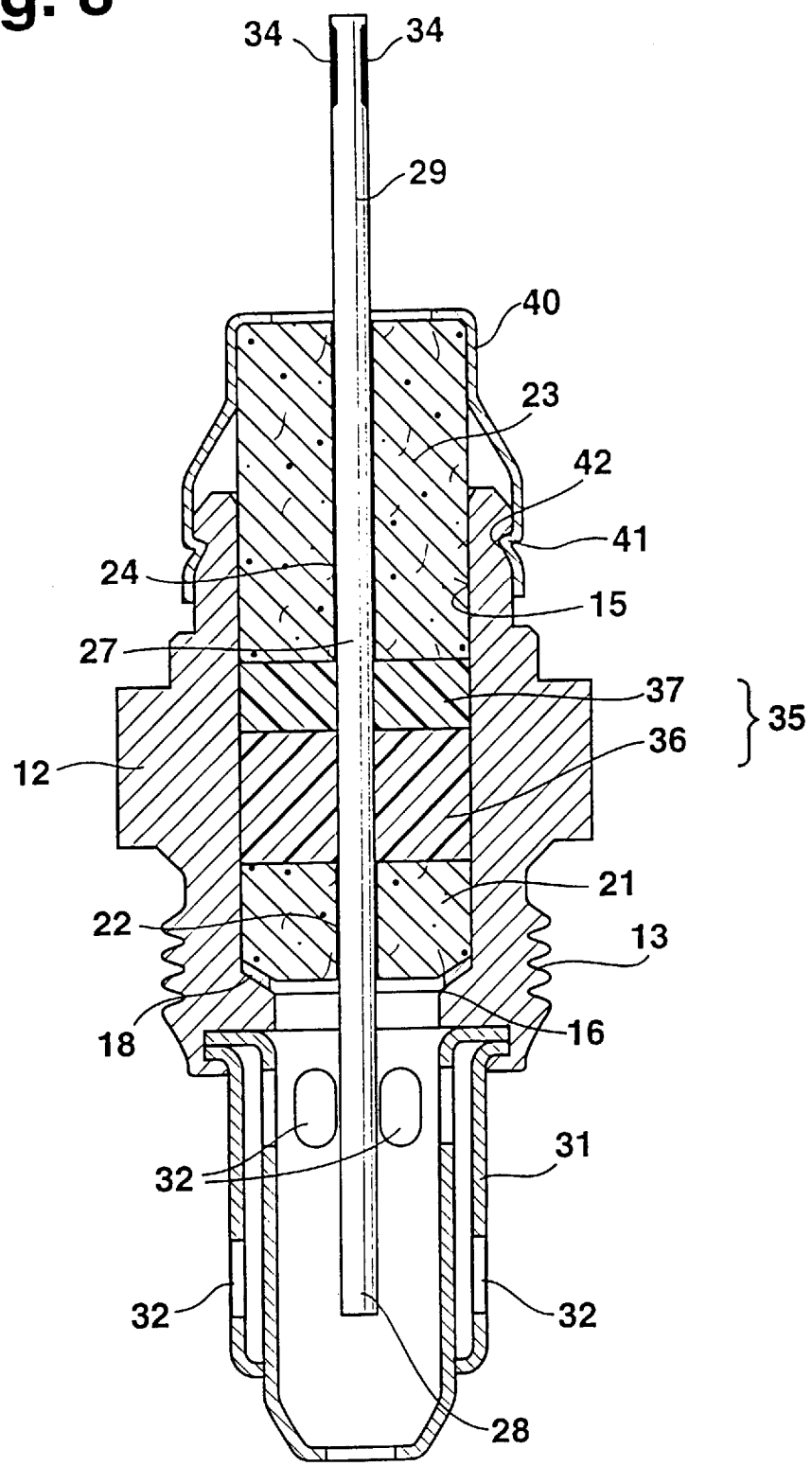

The FIGS. 1, 2 and 3 show a gas sensor 10, for example an electrochemical oxygen sensor with a metallic housing 12, which has a thread 13 as fastening means for installation in a measuring gas tube that is not shown. The housing 12 has a longitudinal bore 15 with a shoulder-type ring surface 16. The shoulder-type ring surface holds, for example, a metallic seal ring 18, on which a molded ceramic part 21 rests on the measuring gas side. The molded ceramic part 21 on the measuring gas side has a continuous opening 22 on the measuring gas side that extends in the direction of the longitudinal bore 15.

Furthermore, a molded ceramic part 23 is also arranged on the connection side in the longitudinal bore 15, at a distance to the molded ceramic part 21 on the measuring gas side. The molded ceramic part 23 on the connection side has a centrally located, continuous opening 24 on the connection side that also extends in the direction of the longitudinal bore 15. The opening 22 on the measuring gas side of the molded ceramic part 21 on the measuring gas side and the connection-side opening 24 of the connection-side molded ceramic part 23 are aligned with each other. A platelike sensor element 27 with an end segment 28 on the measuring gas side and an end segment 29 on the connection side is located in the openings 22, 24.

The measuring gas side end segment 28 of the sensor element 27 projects from the housing 12 and is surrounded by a protective tube 31, which is attached to the housing 12. The protective tube 31 has intake and discharge openings 32 for the gas to be measured. The connection side end segment 29 has connection contacts 34 that also project from the housing 12. The connection contacts 34 are contacted with a contact plug with connecting cables, that is not shown. The end segment 29 on the connection side, which projects from the housing 12, is surrounded by a non-depicted jacket, which protects the end segment 29 from environmental influences.

Between the molded ceramic part 21 on the measuring gas side and the molded ceramic part 23 on the connection side is a sealing arrangement 35, comprising a first seal element 36, a second seal element 37 and a third seal element 38. The first seal element 36 is composed of steatite and rests on the molded ceramic part 21 on the measuring gas side. This is joined by the second seal element 37, which is composed of hexagonal boron nitride. Located above the second seal element 37 is the third seal element 38, which is also composed of steatite. The molded ceramic part 23 on the connection side pushes against the third seal element 38. The contact force of the molded ceramic part 23 on the connection side is generated by a metal sleeve 40. The metal sleeve 40 has, for example, several evenly spaced claws 41 that point toward the inside and engage in notches 42 that are formed into the housing 12. However, it is also conceivable that the metal sleeve 40 is welded to the housing 12.

A second exemplary embodiment is shown in FIG. 2. With this exemplary embodiment, the sealing arrangement 35 consists only of the second seal element 37 and the third seal element 38. The second seal element 37 of boron nitride rests directly on the molded ceramic part 21 on the measuring gas side.

For a third exemplary embodiment according to FIG. 3, the sealing arrangement 35 comprises the first seal element 36 and the second seal element 37. In this case, the molded ceramic part 23 on the connection side pushes directly onto the second seal element 37 of boron nitride.

It has proven useful that the volume of seal elements 36, 38, which are composed of steatite, is approximately twice the volume of the seal element 37 of boron nitride. As a result of this, the thickness of the seal elements 36, 37, 38 according to the embodiment in FIG. 1 is approximately the same. For the two embodiments according to FIGS. 2 and 3, on the other hand, the first seal element 36 or the third seal element 38 is approximately twice as thick in design as the second seal element 37 of boron nitride.

Prior to installing them in the longitudinal bore 15 of the housing 12, the seal elements 36, 38 of steatite are preformed as rings by sintering them at a low temperature of, for example, 500° C. The second seal element 37 of hexagonal boron nitride, on the other hand, is hot-pressed at approximately 2000° C. The ring-shaped seal elements 36, 37, 38 formed in this way are inserted in accordance with the corresponding embodiments into the longitudinal bore 15 that already holds the sensor element 27. The molded ceramic part 23 on the connection side is then placed over the correspondingly designed sealing arrangement 35. The metal sleeve 40 is then fitted onto the molded ceramic part on the connection side. Subsequently, a force is exerted onto the metal sleeve 40, for example by means of a die, which force acts upon the seal elements 36, 37, 38 of the sealing arrangement 35 via the molded ceramic part 23 on the connection side. The prefabricated rings of seal elements 36, 37, 38 are deformed in such a way that the material for the seal elements 36, 37, 38 presses against the sensor element 27 and the housing 12.

It appears that the sealing effect is essentially determined by the hexagonal boron nitride of the second seal element 37. The boron nitride is highly impermeable to gas and fuel as a result of its crystalline structure.

It is essential for achieving an impermeability to gas and fuel over a wide temperature range that a force is present that is constantly exerted by the metal sleeve 40 onto the seal elements 36, 37, 38. As a result of the higher thermal coefficient of expansion of steatite ($8.8 \times 10^{-6} K^{-1}$) as compared to boron nitride (approximately $4.4 \times 10^{-6} K^{-1}$), it is achieved that the contact pressure originating with the metal sleeve 40 acts upon the sealing arrangement 35, even at higher temperatures.

The use of the inventive sealing arrangement 35 is not limited to the sealing of planar sensor elements in metallic housings. It is also conceivable to use such a sealing arrangement 35 for the sealing of so-called finger probes. For that type of use, only the design of the prefabricated rings for the seal elements 36, 37, 38 must be adjusted to the geometry of the longitudinal bore and the supporting surface for housing and finger-shaped sensor elements.

What is claimed is:

1. A seal for a sensor element for a gas sensor for determining the oxygen content in a gas to be measured including exhaust gases of internal combustion engines, the seal comprising:

a metallic housing having defined therein a longitudinal bore;

a sensor element inserted into the longitudinal bore; and a sealing arrangement provided in the longitudinal bore, surrounding at least a portion of the sensor element, and comprised of at least one seal element comprised of steatite and an additional seal element comprised of boron nitride arranged in contact with one another and in a stack having a side near the gas to be measured so that ,when there is one seal element comprised of steatite, the one seal element comprised of steatite is positioned on the side of the stack near the gas to be measured, and so that, when there are two seal elements comprised of steatite, the additional seal element is positioned between the two seal elements comprised of steatite, wherein the at least one seal element comprised of steatite and the additional seal element comprised of boron nitride are inserted into the longitudinal bore of the housing as deformable rings and are pressed-in therein, and wherein, during the pressing-in, the deformable rings are deformed in such a way that the at least one seal element comprised of steatite and the additional seal element comprised of boron nitride are pushed against the sensor element and the housing.

2. The seal according to claim 1, wherein the boron nitride has a crystalline structure which is hexagonal.

3. The seal according to claim 1, wherein the at least one seal element comprised of steatite has a volume, wherein the additional seal element comprised of boron nitride has a volume, and wherein the volume of the at least one seal element comprised of steatite is greater than the volume of the additional seal comprised of boron nitride.

4. The seal according to claim 3, wherein the volume of the at least one seal element comprised of steatite is about twice the volume of the additional seal element comprised of boron nitride.

5. The seal according to claim 1, wherein the sensor element has a side facing the gas to be measured and a connection side, wherein the seal further comprises a molded ceramic part provided within the longitudinal bore and on the side facing the gas to be measured and a molded ceramic part provided within the longitudinal bore and on the connection side and spaced apart from the molded ceramic part provided on the measuring gas side, and wherein the sealing arrangement is positioned between the molded ceramic parts.

6. The seal according to claim 5, further comprising a pressure element provided in the housing and in connection therewith, which pressure element presses on the molded ceramic part provided on the connection side.

7. The sealing according to claim 5, wherein two seal elements comprised of steatite are provided, wherein the sealing arrangement is positioned on top of the molded ceramic part provided on the side of the gas to be measured so that a stack is provided comprised of one sealing element comprised of steatite, the additional seal element comprised of boron nitride, and another sealing element comprised of steatite, and wherein the molded ceramic part provided on the connection side is positioned on top of the stack and exerts pressure thereon.

8. The seal according to claim 5, wherein the sealing arrangement consists of one seal element comprising steatite positioned on top of the molded ceramic part provided on the side of the gas to be measured and the additional seal element comprised of boron nitride on which is positioned the molded ceramic part provided on the connection side so that pressure is exerted thereby on the additional seal element.

9. The seal according to claim 1, wherein deformation of the deformable rings causes conversion of at least a portion of the deformable rings into powder.

10. The seal according to claim 1, wherein the deformable ring of the at least one seal element comprised of steatite is a sintered preformed ring and the deformable ring of the additional seal element comprised of boron nitride is a hot-pressed preformed ring.

* * * * *